United States Patent
Timberlake et al.

(10) Patent No.: US 9,765,204 B2
(45) Date of Patent: *Sep. 19, 2017

(54) HALOGEN FREE HIGH TEMPERATURE POLYAMIDE COMPOSITIONS COMPRISING PHOSPHORUS CONTAINING FLAME RETARDANTS

(71) Applicant: Chemtura Corporation, Middlebury, CT (US)

(72) Inventors: Larry D. Timberlake, West Lafayette, IN (US); Mark V. Hanson, West Lafayette, IN (US); Zachary D. Stockdale, West Lafayette, IN (US)

(73) Assignee: LANXESS Solutions US Inc., Middlebury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/792,833

(22) Filed: Jul. 7, 2015

(65) Prior Publication Data

US 2015/0307690 A1   Oct. 29, 2015

Related U.S. Application Data

(63) Continuation-in-part of application No. 14/592,472, filed on Jan. 8, 2015, which is a continuation-in-part of application No. 14/337,500, filed on Jul. 22, 2014.

(60) Provisional application No. 61/857,741, filed on Jul. 24, 2013, provisional application No. 62/106,098, filed on Jan. 21, 2015.

(51) Int. Cl.

| | |
|---|---|
| *C08K 5/5313* | (2006.01) |
| *C08K 5/3492* | (2006.01) |
| *C07F 9/53* | (2006.01) |
| *C07F 9/6571* | (2006.01) |
| *C07F 9/38* | (2006.01) |
| *C08K 5/00* | (2006.01) |
| *C08K 5/5317* | (2006.01) |
| *C08K 5/5397* | (2006.01) |
| *C08K 5/5333* | (2006.01) |
| *C08K 7/14* | (2006.01) |

(52) U.S. Cl.
CPC .......... *C08K 5/5313* (2013.01); *C07F 9/3808* (2013.01); *C07F 9/5329* (2013.01); *C07F 9/5333* (2013.01); *C07F 9/657172* (2013.01); *C08K 5/0066* (2013.01); *C08K 5/34922* (2013.01); *C08K 5/34928* (2013.01); *C08K 5/5317* (2013.01); *C08K 5/5333* (2013.01); *C08K 5/5397* (2013.01); *C08K 7/14* (2013.01)

(58) Field of Classification Search
CPC ................................ C08K 3/32; C08K 5/5313
See application file for complete search history.

(56) References Cited

U.S. PATENT DOCUMENTS

| | | | |
|---|---|---|---|
| 3,894,986 A | | 7/1975 | Racky et al. |
| 4,972,011 A | | 11/1990 | Richardson et al. |
| 5,053,148 A | * | 10/1991 | von Bonin .............. C04B 38/00 |
| | | | 106/122 |
| 5,780,534 A | | 7/1998 | Kleiner et al. |
| 6,255,371 B1 | | 7/2001 | Schlosser et al. |
| 6,365,071 B1 | | 4/2002 | Jenewein et al. |
| 6,472,448 B2 | | 10/2002 | Witte et al. |
| 6,547,992 B1 | | 4/2003 | Schlosser et al. |
| 7,294,661 B2 | | 11/2007 | Martens et al. |
| 7,531,585 B2 | | 5/2009 | Ozawa et al. |
| 8,445,718 B2 | | 5/2013 | Suwa et al. |
| 2006/0138391 A1 | * | 6/2006 | Drewes .............. C08K 5/34928 |
| | | | 252/601 |
| 2007/0029532 A1 | | 2/2007 | Hansel et al. |
| 2009/0030124 A1 | | 1/2009 | Yin |
| 2011/0021676 A1 | | 1/2011 | Hoerold et al. |
| 2014/0128516 A1 | | 5/2014 | Hoerold et al. |
| 2015/0031805 A1 | | 1/2015 | Stockdale et al. |
| 2015/0141556 A1 | | 5/2015 | Stockdale et al. |

FOREIGN PATENT DOCUMENTS

| | | |
|---|---|---|
| DE | 3833977 | 4/1990 |
| WO | 2005097894 A1 | 10/2005 |
| WO | 2010131678 A1 | 11/2010 |
| WO | 2012045414 | 4/2012 |

OTHER PUBLICATIONS

Polyamide 4/6 Azo Materials Product Data Sheet. Obtained Mar. 31, 2017 at http://www.azom.com/article.aspx?ArticleID=757.*

* cited by examiner

*Primary Examiner* — Lanee Reuther
(74) *Attorney, Agent, or Firm* — Dilworth IP LLC

(57) ABSTRACT

Flame retardants produced by heating certain phosphonic acid salts at temperatures over 200° C. are readily compounded into high temperature polyamides that are processed at temperatures above 270° C. to provide flame retardant, high temperature polyamide compositions.

20 Claims, No Drawings

HALOGEN FREE HIGH TEMPERATURE POLYAMIDE COMPOSITIONS COMPRISING PHOSPHORUS CONTAINING FLAME RETARDANTS

This application is a continuation-in-part of U.S. patent application Ser. No. 14/592,472, filed Jan. 8, 2015, which is a continuation-in-part of U.S. patent application Ser. No. 14/337,500, filed Jul. 22, 2014, which claims priority to U.S. Prov. Appl. No. 61/857,741, filed Jul. 24, 2013; and further, this application claims benefit under 35 USC 119(e) of U.S. Prov. Appl. No. 62/106,098 filed on Jan. 21, 2015.

Flame retardant polymer compositions are provided comprising high temperature polyamides and flame retardants that were obtained by heating certain phosphonic acid salts at temperatures over 200° C., which compositions are readily processed and have excellent flame retardant properties.

BACKGROUND OF THE INVENTION

Polymers with high melting points, such as high temperature polyamides, are highly valued due to their excellent mechanical properties and chemical resistance. Such high temperature polyamides have found use in automotive parts, electric/electronic components, mechanical components, and many other applications due to the improved thermal stability properties that this type of polymers exhibit.

For example, high temperature polyamides are used extensively in compositions which make possible the production of molded articles with excellent dimensional stability at high temperatures, e.g., in the electrical and electronics industry. Molding compositions of this type are demanded, for example, in the electronics industry for producing components which are mounted on printed circuit boards according to the so-called surface mounting technology, SMT. Components in such applications must withstand temperatures of up to 270° C. for short periods of time without dimensional change and retain very good flame-retardant properties. Very thin-walled components are often needed in the electronics industry because of miniaturization, and a flammability classification according to UL94 of V0 at 0.4 mm is required.

Many known flame retardants, including many halogenated materials, are not suitable under these processing conditions because they are too volatile, not sufficiently thermally stable, have an adverse effect on processing and physical properties, etc. Some flame retardants need to be used at undesirably high concentrations in order to provide the required flame retardant activity.

Salts of phosphorus containing acids are known flame-retardant additives, in particular for thermoplastic polymers. U.S. Pat. No. 3,894,986 discloses flame retardant thermoplastic polyesters containing alkali salts of phosphonic acids, e.g., the mono sodium salt of ethane-phosphonic acid or a sodium salt of a mono-methyl ester of an alkane-phosphonic acid. U.S. Pat. No. 4,972,011 discloses aluminum salts of alkylphosphonic acids or mono-alkyl esters of alkane-phosphonic acids, i.e., salts of compounds of formula (Ia), wherein R is for example methyl, ethyl, propyl or isopropyl etc., unsubstituted or substituted by one or more halo or hydroxy groups; and R' is hydrogen, methyl, ethyl, propyl, or isopropyl.

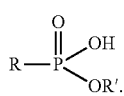

(Ia)

DE 3833977 discloses metal salts of compounds of formula (Ia) prepared from reactions of dimethylmethylphosphinate and metal oxides or hydroxides in water at high pressures and temperatures from 120 to 200° C.; reactions run in aqueous solution under elevated pressures at temperatures up to 190° C. in an autoclave are exemplified.

Salts of phosphinic acids, i.e., compounds of formula (II) wherein $R_1$ and $R_2$ are alkyl or carbon based aromatic, are also known flame-retardant additives for thermoplastic polymers.

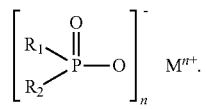

(II)

Salts wherein M is selected from Mg, Ca, Al, Sb, Sn, Ge, Ti, Zn, Fe, Zr, Ce, Bi, U, Na, K or protonated nitrogen base are known. For example, U.S. Pat. Nos. 5,780,534 and 6,013,707 disclose that calcium phosphinates and aluminum phosphinates of Formula (II) are particularly effective in polyester, for example, calcium and aluminum salts of dimethylphosphinic acid, ethylmethylphosphinic acid, diethylphosphinic acid, n-propylmethylphosphinic acid, n-propylethylphosphinic acid, di-n-propylphosphinic acid, diisopropylphosphinic acid or diphenylphosphinic acid.

U.S. Pat. No. 6,255,371 discloses a flame retardant combination comprising, A) a phosphinate of formula (II) above, e.g., a diethyl phosphinate where M is calcium, magnesium, aluminum and/or zinc, and B) condensation or reaction products of melamine e.g., melamine polyphosphate, melam polyphosphate and melem polyphosphate. U.S. Pat. No. 6,547,992 discloses a flame retardant combination for thermoplastic polymers comprising phosphinates and small amounts of inorganic and/or mineral compounds which do not contain nitrogen. WO 2012/045414 discloses a flame retardant composition comprising A) a phosphinic salt of the formula (II) above wherein M is selected from Mg, Ca, Al, Sb, Sn, Ge, Ti, Zn, Fe, Zr, Ce, Bi, Li, Na, K or a protonated nitrogen base; B) a metal salt of phosphorous acid; and other optional components.

U.S. Pub. Pat. Appl. 2009/0030124 discloses flame resistant, semiaromatic, high temperature polyamide resin compositions comprising phosphinate or diphosphinate flame retardant and zinc borate that have reduced corrosion effects on melt processing equipment. U.S. Pat. No. 7,294,661 discloses flame resistant polyamide resin compositions for molded articles comprising aromatic high temperature polyamides with phosphinate and/or diphosphinate flame retardant and, optionally, glass fibers. U.S. Pat. No. 7,723,411 discloses flameproof, high temperature polyamide molding compositions comprising a semi-aromatic, high temperature, partially crystalline polyamide and a flame retardant containing a phosphinic acid salt and/or a diphosphinic acid salt.

U.S. Pub. Pat. Appl. 2011/0021676 discloses that mixtures of phosphinate salts of Al, Mg, Ca, Ti, Zn, or Na with certain metal soaps and metal salts are effective flame retardants in polyesters and polyamides, inclusive of semi-aromatic high-temperature polyamides, and exhibit a lower level of wear on materials and higher levels of flowability than the phosphinates of the metals when these are used alone and can be processed at high temperatures without polymer degradation or discoloration. For example, a polyamide composition comprising a mixture of aluminum diethylphosphinate and zinc diethylphosphinate exhibits less corrosion with a simultaneous improvement in flowability when compared to a polyamide composition comprising only aluminum diethylphosphinate Despite the above disclosures, many of these flame retardants are still not completely suitable for demanding high temperature polyamide applications, such as extrusion and molding of high temperature polyamides. For example, U.S. Pub. Pat. Appl. 20140128516 discloses that polymer compositions comprising many phosphorus acid salts form mold deposits during injection molding, exude during storage under warm, humid conditions, and can give off emissions during compounding. To overcome this difficulty, certain monoarylphosphinic salts are disclosed that when used with selected nitrogen-containing synergists or a phosphorus-nitrogen flame retardant, and optionally with a further stabilizer, are effective flame retardant systems for polymers exhibiting neither polymer degradation nor deposits or exudate.

While many phosphinate and phosphonate salts are said to be thermally stable, this is of course a relative term. As disclosed in US 2007/0029532, decomposition of phosphonic acid salts is well known at temperatures encountered during processing of polyesters and polyamides, damaging the polymers in the process.

U.S. Pat. No. 5,053,148 discloses the preparation of heat resistant foams useful, e.g., as electrical and/or heat insulation materials, obtained by heating polymer compositions, such as polyamide compositions, comprising metal phosphonates or metal phosphonate precursors to temperatures of above 200° C. The foams are seemingly produced by a "foaming process" related to the action, presumably decomposition, of the salts at high temperature. Nothing in U.S. Pat. No. 5,053,148 addresses or refutes the disclosure of US 2007/0029532 that decomposition of such phosphonic acid salts at high temperature gives "brittle compositions which are unusable" as an engineering thermoplastic.

There is still a need for flame retardants with greater efficiency at lower additive concentrations and improved processability for use in preparing flame retardant high temperature polyamide compositions. Copending U.S. patent application Ser. No. 14/337,500 discloses that heating certain alkylphosphonic acid metal salts, such as aluminum salts, calcium salts, zinc salts etc., at temperatures in excess of 200° C. transforms the salts into different materials that are thermally stable at temperatures above 400° C. and can be incorporated onto thermoplastic polymer resins without the adverse impact on physical properties of the polymer seen with many of the salts described above.

It has now been found that the thermally stable products obtained by heating certain alkylphosphonic acid metal salts, such as aluminum salts, calcium salts, zinc salts etc., at temperatures in excess of 200° C. can be incorporated into high temperature polyamides at temperatures above 270° C. without adversely impacting the resulting physical properties of the polymer composition obtained. It has also been found that a lower concentration of the present flame retardants is required to obtain desired flame retardancy in these high temperature polyamides than is needed when incorporated into lower melting polyamides such as nylon 66.

SUMMARY OF THE INVENTION

A flame retardant composition comprising:
a) a high temperature polyamide resin, and
b) from 1% to 24%, by weight based on the total weight of the flame retardant composition, of a phosphorus containing flame retardant material obtained by heating at temperatures of 200° C. or higher, e.g., 220° C. or higher, generally at temperatures of 250° C. or higher, e.g. from about 250° C. to about 400° C. or from about 260° C. to about 360° C., one, or more than one, phosphonic acid salt, i.e., compounds of formula (I)

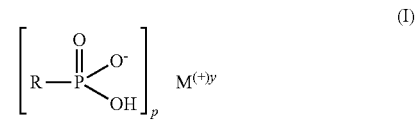

wherein R is an alkyl, aryl, alkylaryl or arylalkyl group, p is a number of from 1 to 7, e.g., from 1 to 4, e.g., 1, 2, 3 or 4, M is a metal, y is a number of from 1 to 7, e.g., from 1 to 4, e.g., 1, 2, 3 or 4, often 2 or 3, so that $M^{(+)y}$ is a metal cation where (+)y represents the charge formally assigned to the cation. For example, flame retardant materials produced in copending U.S. patent application Ser. Nos. 14/337,500 and 14/592,472.

Typically, a lower concentration of flame retardant of the invention is required for the desired flame retardant activity in the present high temperature polyamides than is required when the same flame retardant is used in polyamides that melt at temperatures below 270° C.

Embodiments of the invention also provide articles comprising flame retardant aromatic and semi-aromatic polyamide compositions comprising the flame retardant material of component b), methods for preparing the compositions and methods for shaping the articles Because not all polymers have a well defined melting point, the terms "melts at", "melting at" or "melting above" as used herein refers to the low end of the polymer's melting range.

DESCRIPTION OF THE INVENTION

Flame retardants useful as component b) in the high temperature polyamide compositions of the present invention are materials obtained by heating one or more compounds of formula (I) at temperatures of 200° C. or higher. These flame retardant materials are significantly more thermally stable than the compounds of formula (I) from which they are formed. As a result, the flame retardants used in the invention can be readily incorporated into polymers processed at high temperatures, such as polyamides, to produce compositions with excellent physical properties. As shown, for example, in US 2007/0029532 and copending U.S. patent application Ser. No. 14/337,500, attempts to incorporate the compounds of formula (I) directly into polyamide at elevated temperatures caused the polymer degradation producing a brittle material which could not be molded.

Thus, the materials useful as component b) in the high temperature polyamide compositions of the present invention are the products produced by heating at temperatures of 200° C. or higher, e.g., 220° C., often 250° C. or higher, typically in the absence of other materials, one, or more than one, phosphonic acid salt, i.e., compounds of formula (I)

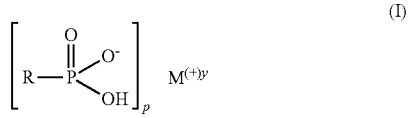

(I)

wherein R is an alkyl, aryl, alkylaryl or arylalkyl group, p is a number of from 1 to 7, e.g., from 1 to 4, e.g., 1, 2, 3 or 4, M is a metal, y is a number of from 1 to 7, e.g., from 1 to 4, e.g., 1, 2, 3 or 4, often 2 or 3, so that $M^{(+)y}$ is a metal cation where (+)y represents the charge formally assigned to the cation.

For example, in formula (I), $M^{(+)y}$ where y is 1 represents a mono-cation such as $Li^+$, $Na^+$ or $K^+$, $M^{(+)y}$ where y is 2 represents a di-cation such as $Mg^{++}$, $Ca^{++}$ or $Zn^{++}$ and the like, $M^{(+)y}$ where y is 3 represents a tri-cation such as $Al^{+++}$, etc. As is common with organometallic species, the formulae are idealized and the starting materials may include complex salts or salts where certain atomic valences are shared such as where a single oxygen anion is shared between two metal cations, etc. Typically, the starting salt is charged balanced, that is, a compound of formula (I) wherein p=y, e.g., when $M^{(+)y}$ is $Na^+$, p is 1, when M is $Al^{+++}$ p is 3, etc.

Not wanting to be bound by theory, analytical data suggest that the material generated by heating compounds of formula (I) at the listed temperature comprises a compound or a mixture of compounds one or more of which is believed to be generically represented by the empirical formula (IV):

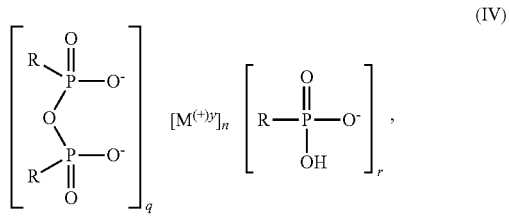

(IV)

wherein R and M are as defined for formula (I), q is a number of from 1 to 7, e.g., 1, 2 or 3, r is a number from 0 to 5, e.g., 0, 1 or 2, often 0 or 1, y is a number of from 1 to 7, e.g., from 1 to 4, e.g., 1, 2, 3, or 4, and n is 1 or 2, provided that 2(q)+r=n(y). It is believed that more than one compound is typically present in the material so generated.

The phosphonic acid salts of formula (I) are known and various methods for their preparation are described in the art. For example, US 2006/0138391 discloses compounds of formula (I) wherein R is hydrogen, $C_{1-18}$ alkyl, $C_{5-6}$ cycloalkyl, $C_{2-6}$ alkenyl, $C_{5-10}$ aryl, or $C_{7-11}$ aralkyl, which alkyl, alkenyl, aryl, or aralkyl can be unsubstituted or substituted by halogen, hydroxyl, amino, $C_{1-4}$ alkylamino, di-$C_{1-4}$ alkylamino, $C_{1-4}$ alkoxy, carboxy or $C_{2-5}$ alkoxycarbonyl; and M can be selected from, e.g., Group IA, IB, IIA, IIB, IIIA, IVA, VA or VII of the Periodic Table, for example Li, K, Na, Mg, Ca, Ba, Zn, Ge, B, Al, Cu, Fe, Sn or Sb, etc. It is noted that in US 2006/0138391 none of the compounds corresponding to the formula (I) above were heated above 200° C. or compounded into a polymer resin at elevated temperature.

In some embodiments of the invention, the salts of formula (I) comprise compounds wherein R is $C_{1-12}$ alkyl, $C_{6-10}$ aryl, $C_{7-18}$ alkylaryl, or $C_{7-18}$ arylalkyl group, wherein said groups are further substituted as described in US 2006/0138391, but often R is unsubstituted $C_{1-12}$ alkyl, $C_{6-10}$ aryl, $C_{7-18}$ alkylaryl, or $C_{7-18}$ arylalkyl. For example, R is substituted or unsubstituted, typically unsubstituted, $C_{1-6}$ alkyl, $C_6$ aryl, $C_{7-10}$ alkylaryl, or $C_{7-12}$ arylalkyl, e.g., $C_{1-4}$ alkyl, $C_6$ aryl, $C_{7-19}$ alkylaryl, or $C_{7-10}$ arylalkyl.

While in the most general embodiments of the invention $M^{(+)y}$ may be almost any metal cation, M is generally selected from U, K, Na, Mg, Ca, Ba, Zn, Zr, Ge, B, Al, Si, Ti, Cu, Fe, Sn or Sb, for example, e.g., Li, K, Na, Mg, Ca, Ba, Zn, Zr, B, Al, Si, Ti, Sn or Sb, in many embodiments M is Li, K, Na, Mg, Ca, Ba, Zn, Zr, B, Al, Sn or Sb, and in certain embodiments M is Al, Zn or Ca. For example, excellent results are achieved when M is Al or Ca.

R as alkyl is a straight or branched chain alkyl group having the specified number of carbons and includes e.g., unbranched alky such as methyl, ethyl, propyl, butyl, pentyl, hexyl heptyl, octyl, nonyl, decyl, undecyl, dodecyl, and unbranched alkyl such as iso propyl, iso-butyl, sec-butyl, t-butyl, ethyl hexyl, t-octyl and the like. For example, R as alkyl is methyl, ethyl, propyl, iso propyl, butyl, iso butyl, sec-buty, t-butyl, often R is methyl, ethyl, propyl or isopropyl, for example methyl.

Typically when R is aryl it is phenyl or naphthyl, for example, phenyl. Examples of R as alkylaryl include phenyl substituted by one or more alkyl groups, for example groups selected from methyl, ethyl, propyl, isopropyl, butyl, iso butyl, sec-buty, t-butyl, and the like. Examples of R as arylalkyl, include for example, benzyl, phenethyl, styryl, cumyl, phenpropyl and the like.

In one embodiment R is methyl, ethyl, propyl, isopropyl, phenyl or benzyl, e.g., methyl or phenyl.

In certain embodiments, for example, the starting material is one or more compounds of formula (I) wherein R is methyl, ethyl, propyl, isopropyl, benzyl or phenyl, M is Al, Zn or Ca, and p is 2 or 3. In one particular embodiment R is methyl, ethyl, propyl, isopropyl, or phenyl, p=3 and M is Al; in another particular embodiment R is methyl, ethyl, propyl, isopropyl, or phenyl, p=2 and M is Zn or Ca, e.g., Ca.

Typically, thermal treatment of a compound of formula (I) as above generates a material comprising more than one compound, at least one of which is believed to be generically represented by the empirical formula (IV) and complex dehydration products thereof. As is common with organometallic species, the formula (IV) is idealized and the product may include polymeric salts, complex salts, salts where certain atomic valences are shared, etc.

For example, when M is aluminum, i.e., when a compound of formula (I) wherein M is Al is heated according to the invention, elemental analysis suggests the formation of a product having an empirical formula (IV) wherein q is 1, r is 1, n is 1 and y is 3.

When formed from a compound of formula (I) wherein one R group and one metal is present, a mixture of compounds typically forms comprising at least one compound of formula (IV), wherein said mixture and said compound or compounds of formula (IV) comprise the one R group and the one metal. In some embodiments of the invention, the flame retardant material comprises a mixtures of compounds wherein more than one R group and/or more than one metal is present, and wherein a mixture of compounds of formula (IV) comprising more than one R group and/or more than one metal is present. Flame retardants of the invention comprising compounds containing more than one R groups and/or more than one metal can be formed in various ways.

In a first method, which can be called the intermediate salt complex method, one or more phosphonic acid compounds are treated with one or more appropriate metal compounds to give an intermediate salt complex corresponding to formula (I), which complex comprises multiple values for R and/or M. Often the metal, or at least one of the metals used in forming the intermediate salt complex will be a bidentate or polydentate metal and more than one intermediate complex may be formed. This salt complex is then heat-treated as described above to obtain a flame retardant material comprising:
a) at least one compound corresponding to formula (IV) having more than one than one R group and/or more than one M group, and/or
b) a mixture of compounds corresponding to formula (IV) are present said mixture comprising compounds with different R groups and/or different M groups.

Alternatively, in a second method, which can be called the intimate salt mixture method, two or more metal phosphonic acid salts of formula (I) are brought together to form an intimate salt mixture comprising salts which have differing values for R and/or M. This mixture is then subjected to heat treatment described above to obtain a flame retardant material comprising:
a) at least one compound corresponding to formula (IV) having more than one than one R group and/or more than one M group, and/or
b) a mixture of compounds corresponding to formula (IV) are present said mixture comprising compounds with different R groups and/or different M groups.

A third method for obtaining flame retardant materials of the invention comprising compounds of formula (IV) having multiple values for R and/or M comprises separately heating two or more individual metal phosphonic acid salts of formula (I), which differ by having different values for R and/or M, as described above to separately obtain two or more flame retardant materials of the invention, which are subsequently mixed together to form a blended flame retardant composition.

The exact composition the mixtures obtained by the preceding three processes, i.e., the intermediate salt complex method, the intimate salt mixture method, and the blending of separately obtained flame retardant materials, will generally be different even when starting from the same phosphonic acid compounds and metals. Thus, differences in physical characteristics, stability, miscibility and performance for the products of the different methods are generally encountered.

Generally, the selected phosphonic acid metal salt or mixture of salts used as starting material for the flame retardant is heated in the absence of other materials.

While many known flame retardants have drawbacks when used in polyamides processed at temperatures in excess of 270° C., such as degradation of polymer, flame retardant or both, the flame retardant material of the present invention can be compounded into these resins under highly demanding processing conditions without comprising the physical properties of the resin, the chemical properties of the resin, or the integrity of the flame retardant.

The high temperature polyamide of the present invention is a polyamide that melts above 270° C., typically at temperatures of 280° C. or higher. Generally, the high temperature polyamides of the invention are aromatic and semi-aromatic polyamides, however aliphatic polyamide 46, which has a melting point higher than typical aliphatic polyamides, is also included as a polyamide resin of the invention. Examples of high temperature polyamides include the aliphatic polyamide 46 and aromatic or semi-aromatic polyamide resins such as polyamide 4T, polyamide MXD,6, polyamide 12,T, and the like. More than one high temperature polyamide may be present and it is possible that the high temperature polyamide is blended with other polymers including minor amounts of polyamides that melt at lower temperatures provided the melting point of the blend remains above 270° C. or 280° C.

Aromatic and semi-aromatic polyamides are homopolymers, copolymers, terpolymers, or higher polymers that are derived from monomers containing aromatic groups. Examples of monomers containing aromatic groups are terephthalic acid and its derivatives, isophthalic acid and its derivatives, and m-xylylenediamine. Generally about 5 to about 75 mole percent of the monomers used to make an aromatic or semi-aromatic polyamide contain aromatic groups, often about 10 to about 55 mole percent of the monomers contain aromatic groups.

Semiaromatic or aromatic polyamide may be derived from dicarboxylic acids or their derivatives, such one or more of adipic acid, sebacic acid, azelaic acid, dodecanedoic acid, 1,4-cyclohexane dicarboxylic acid, terephthalic acid, isophthalic acid or their derivatives and other aliphatic and aromatic dicarboxylic acids and aliphatic $C_6$-$C_{20}$ alkylenediamines, aromatic diamines, and/or alicyclic diamines. Diamines include hexamethylenediamine; 2-methylpentamethylenediamine; trimethylhexamethylenediamine; 2-methyloctamethylene diamine; 1,8-diaminooctane; 1,9-diaminononane; 1,10-diaminodecane; 1,12-diaminododecane; and m-xylylenediamine. It may also be derived from one or more lactams or amino acids such as 11-aminododecanoic acid, caprolactam, and laurolactam.

Examples aromatic or semi-aromatic polyamides include polyamide 4T, poly(m-xylylene adipamide) (polyamide MXD,6), poly(dodecamethylene terephthalamide) (polyamide 12,T), poly(decamethylene terephthalamide) (polyamide 10,T), poly(nonamethylene terephthalamide) (polyamide 9,T), hexamethylene adipamide/hexamethylene terephthalamide copolyamide (polyamide 6,T/6,6), hexamethylene terephthalamide/2-methylpentamethylene terephthalamide copolyamide (polyamide 6,T/D,T); hexamethylene adipamide/hexamethylene terephthalamide/hexamethylene isophthalamide copolyamide (polyamide 6,6/6,T/6,I); poly(caprolactam-hexamethylene terephthalamide) (polyamide 6/6,T); hexamethylene terephthalamide/hexamethylene isophthalamide (6,T/6,I) copolymer, and the like.

As stated above, the polyamide component (a) may further comprise one or more lower melting aliphatic and/or alicyclic polyamides, derived, for example, from monomers such as adipic acid, sebacic acid, azelaic acid, dodecanedoic acid, 1,4-cyclohexane dicarboxylic acid, or their derivatives and the like, aliphatic $C_6$-$C_{20}$ alkylenediamines, alicyclic diamines, lactams, and amino acids, including for example, 1,4-cyclohexane diamine, di-(4-diaminocyclohexyl)-methane, di-(3-methyl-4-aminocyclohexyl)-methane, hexamethylenediamine; 2-methylpentamethylenediamine; trimethylhexamethylenediamine; 2-methyloctamethylene diamine; 1,8-diaminooctane; 1,9-diaminononane; 1,10-diaminodecane; 1,12-diaminododecane; 11-aminododecanoic acid, caprolactam, and laurolactam. When present, such aliphatic polyamides are a minor component of the resin, e.g., less than 40 wt %, typically less than 20 wt % often less than 10 wt %, e.g., 5 wt % or less, as significant levels of some aliphatic resins will lower the melting point to less than, e.g., 280° C.

In some particular embodiments, the aromatic or semi-aromatic polyamide is composed of terephthalic acid (TPS), isophthalic acid (IPS) and hexamethyl diamine or from terephthalic acid, adipic acid and hexamethyl diamine, for example, hexamethylene diamine and approximately 70:30 TPS:IPS or 55:45 TPS:adipic acid.

Despite the high melting points of the high temperature polyamides and the need to process and mold them at similarly high temperatures, the flame retardant polyamide compositions possess excellent mechanical properties, moldability, and chemical resistance particularly useful in automotive parts, electric/electronic components, mechanical components, and many other applications. For example, in one particular embodiment the composition of the invention provides molded articles for the electrical and electronics industry, including very thin-walled components, having excellent dimensional stability at high temperatures and very good flame-retardant properties, such as components that are mounted on printed circuit boards according to the so-called surface mounting technology, SMT.

When used as the sole flame retarding component of a high temperature polyamide composition the inventive flame retardant may be present in a concentration of from about 1 to about 24%, e.g., 1 to 20%, 1 to 15% or 1 to 12%, by weight based on the total weight of the final composition. Typically, when used as the sole flame retardant there will be at least 2% of the inventive material present, for example at least 3%, or at least 5%. In one embodiment, the inventive flame retardant is present in amounts of from 5 to 10%. When used in combination with other flame retardants or flame retardant synergists, less of the inventive material should be needed.

Any known compounding techniques useful for such high melting polymers may be used to prepare the flame retardant polymer composition of the invention, for example, the flame retardant may be introduced into molten polymer by blending, extrusion, fiber or film formation etc. Often, once prepared, the flame retardant polymer composition of the invention is further processed or shaped, e.g., using various molding techniques.

The flame retardant of the invention may be used with a variety of other flame retardants, flame retardant synergists or flame retardant adjuvants as known in the art. Particular attention is required regarding the thermal stability of the synergists or adjuvants to ensure that they are compatible with the processing conditions for high temperature polyamides.

For example, the flame retardant of the invention may be formulated with one or more materials selected from:
carbon black, graphite, carbon nanotubes, silicones; polyphenylene ether (PPE), phosphine oxides and polyphosphine oxides, e.g., benzylic phosphine oxides, poly benzylic phosphine oxides and the like;
certain melamine derivatives and condensation products, melamine salts such as, but not limited to, melamine borate, melamine metal phosphates, and the like;
inorganic compounds including days, metal salts such as hydroxides, oxides, oxide hydrates, borates, carbonates, sulfates, phosphates, phosphites, hypophosphites, silicates, mixed metal salts, etc., e.g., talc and other magnesium silicates, calcium silicate, aluminosilicate, aluminosilicate as hollow tubes (DRAGONITE), calcium carbonate, magnesium carbonate, barium sulfate, calcium sulfate, HALLOYSITE or boron phosphate, calcium molybdate, exfoliated vermiculite, zinc stannate, zinc hydroxystannate, zinc sulfide and zinc borate, zinc molybdate (KEMGARD 911A/B), zinc phosphate (KEMGARD 981), magnesium oxide or hydroxide, aluminum oxide, aluminum oxide hydroxide (Boehmite), aluminum trihydrate, silica, tin oxide, antimony oxide (III and V) and oxide hydrate, titanium oxide, and zinc oxide or oxide hydrate, zirconium oxide and/or zirconium hydroxide and the like.

Unless otherwise specified, in the context of the present application, the term "phosphate" when used as a component in a "phosphate salt", such as in metal phosphate, melamine phosphate, melamine metal phosphate, etc., refers to a phosphate, hydrogen phosphate, dihydrogen phosphate, pyrophosphate, polyphosphate, or a phosphoric acid condensation products anion or polyanion.

Likewise, unless otherwise specified, in the context of the present application, the term "phosphite" when used as a component in a "phosphite salt", such as in metal phosphite, etc., refers to a phosphite or hydrogen phosphite.

The flame retardant of the invention may also be formulated with other flame retardants such as alkyl or aryl phosphine oxide flame retardants, and salts of alkyl or aryl phosphinic acid. One particular embodiment provides a synergistic mixture of the flame retardant of the invention and a phosphinic salt of formula (II), e.g., an aluminum tris(dialkylphosphinate).

Thus, in many embodiments the flame retardant polymer composition according to the invention comprises the polymer (a), the flame retardant (b), and further comprises (c) one or more additional flame retardants, and/or one or more synergists or flame retardant adjuvants.

For example, in some embodiments the flame retardant polymer composition comprises one or more additional flame retardants, e.g., phosphine oxide flame retardants, alkyl or aryl phosphonates, or salts of alkyl or aryl phosphinates, e.g., an aluminum tris(dialkylphosphinate) such as aluminum tris(diethylphosphinate).

In some embodiments the flame retardant polymer composition comprises one or more synergists or flame retardant adjuvants, e.g., melamine, melamine derivatives and condensation products, melamine salts, phosphine oxides and polyphosphine oxides, metal salts such as hydroxides, oxides, oxide hydrates, borates, phosphates, phosphites, silicates and the like, e.g. aluminum hydrogen phosphite, melem or a melamine metal phosphate, e.g., a melamine metal phosphate wherein the metal comprises aluminum, magnesium or zinc. In particular embodiments the one or more additional flame retardant, synergist or flame retardant adjuvant comprises an aluminum tris(dialkylphosphinate), aluminum hydrogen phosphite, methylene-diphenylphosphine oxide-substituted polyaryl ether, xylylenebis (diphenylphosphine oxide), 4,4'-bis(diphenylphosphinylmethyl)-1,1'-biphenyl, ethylene bis-1,2-bis-(9,10-dihydro-9-oxy-10-phosphaphenanthrene-10-oxide)ethane, melam, melem, or dimelamine zinc pyrophosphate.

One particular embodiment is to a synergistic mixture comprising the flame retardant of the invention and aluminum tris(diethylphosphinate).

For example, the flame retardant of the invention may be combined with an additional flame retardant, synergist or adjuvant in a range of 100:1 to 1:100 by weight of inventive flame retardant to the total weight of additional flame retardant, synergist and adjuvant. Depending on the additional flame retardant, synergist or adjuvant, excellent can be obtained using a range of 10:1 to 1:10 by weight of flame retardant to additional flame retardant, synergist and/or adjuvant, for example, weight ratios ranging from 7:1 to 1:7, 6:1 to 1:6, 4:1 to 1:4, 3:1 to 1:3 and 2:1 to 1:2 are used to good benefit. The inventive flame retardant is typically the majority component in such a combination, e.g., a 10:1 to 1.2:1 ratio or a 7:1 to 2:1 ratio by weight of the inventive flame retardant material to additional flame retardant, synergist and/or adjuvant, but the inventive material can also be the minor component of the mixture, e.g., a 1:10 to 1:1.2 ratio or a 1:7 to 1:2 ratio of flame retardant to additional flame retardant, synergist and/or adjuvant synergist.

The flame retardant polymer composition of the invention will also typically contain one or more of the common stabilizers or other additives frequently encountered in the art such as phenolic antioxidants, hindered amine light stabilizers (HALS), the ultraviolet light absorbers, phosphites, phosphonites, alkaline metal salts of fatty acids, hydrotalcites, metal oxides, borates, epoxidized soybean oils, the hydroxylamines, the tertiary amine oxides, lactones, thermal reaction products of tertiary amine oxides, thiosynergists, basic co-stabilizers, for example, melamine, melem etc., polyvinylpyrrolidone, dicyandiamide, triallyl cyanurate, urea derivatives, hydrazine derivatives, amines, polyamides, polyurethanes, hydrotalcites, alkali metal salts and alkaline earth metal salts of higher fatty acids, for example, Ca stearate, calcium stearoyl lactate, calcium lactate, Zn stearate, Zn octoate, Mg stearate, Na ricinoleate and K palmirate, antimony pyrocatecholate or zinc pyrocatecholate, nucleating agents, clarifying agents, etc.

Other additives may also be present, for example, plasticizers, lubricants, emulsifiers, pigments, dyes, optical brighteners, other flameproofing agents, anti-static agents, blowing agents, anti drip agents, e.g., PTFE, and the like.

Optionally the polymer may include fillers and reinforcing agents, for example, calcium carbonate, silicates, glass fibers, talc, kaolin, mica, barium sulfate, metal oxides and hydroxides, carbon black and graphite. Such fillers and reinforcing agents may often be present at relatively high concentrations, including formulations where the filler or reinforcement is present in concentrations of over 50 wt % based on the weight of the final composition. More typically, fillers and reinforcing agents are present from about 5 to about 50 wt %, e.g., about 10 to about 40 wt % or about 15 to about 30 wt % based on the weight of the total polymer composition.

For example, aromatic or semi-aromatic polyamide compositions of the invention may, but not always, comprise from 5 to 50% by weight, and sometimes higher amounts, of fibrous or particulate fillers, or a mixture of these, for example, glass fibers, and in many embodiments will also comprise a synergist, provided that the synergists is compatible with the processing conditions, such as a melamine synergist such as dimelamine phosphate, melamine pyrophosphate, melamine polyphosphates, melam polyphosphates, melem polyphosphates, and/or melon polyphosphates, and/or melamine condensates, such as melam, melem, and/or melon, along with other optional additives as described above. As in all cases, the thermal stability of any additive needs to be considered before inclusion in the present compositions.

Particular embodiments of the invention include a flame retardant polymer composition comprising:
 a) a high temperature polyamide,
 b) from 1% to 24%, e.g., 5% to 20% or 5 to 12%, by weight of the flame retardant material obtained by a process comprising heating at temperatures of about 200° C. or higher from about 0.01 hour to about 20 hours one or more than one compound of formula (I);

A flame retardant polymer composition comprising:
 a) from 30-80% by weight of the polyamide above,
 b) from 1% to 24%, e.g., 5% to 20% or 5 to 12%, by weight of the flame retardant material above,
 (c) from 1% to 20% e.g., 2% to 15%, by weight of one or more additional flame retardants, one or more synergists and/or one or more flame retardant adjuvants, and
 d) optionally from 0.5 to 30%, e.g., 1 to 20% or 2% to 15%, by weight of other additives;

A flame retardant polymer composition comprising:
 a) from 30-80% by weight of the polyamide above,
 b) from 1% to 24%, e.g., 5% to 20% or 5 to 12%, by weight of the flame retardant material above,
 (c) from 0% to 20% by weight of one or more additional flame retardants, one or more synergists and/or one or more flame retardant adjuvants, and
 d) from 0.5 to 30%, e.g., 1 to 20% or 2% to 15%, by weight of other additives;

A flame retardant polymer composition comprising:
 a) from 30-70% by weight of the polyamide above,
 b) from 1% to 24%, e.g., 5% to 20% or 5 to 12%, by weight of the flame retardant material above,
 (c) optionally, from 1% to 20%, e.g., 2% to 15% by weight of one or more additional flame retardants, one or more synergists and/or one or more flame retardant adjuvants
 d) from 5 to 50%, e.g., from 10 to 40% or 15 to 35% by weight of a glass reinforcing agent, and
 e) optionally 0.5 to 20%, e.g., 1 to 10%, by weight other additives.

The compositions of the invention are useful in a wide variety of articles including moldings, films, filaments and fibers, which may be produced in any of the methods known in the art. In one particular embodiment articles are formed from the compositions of the invention by injection molding, blow molding, extrusion, pressing or thermoforming. Examples of such articles include housings, electrical connectors and connector housings and cases, breaker housings, and contactor housings.

EXAMPLES

Example 1—Flame Retardant from Methylphosphonic Acid Aluminum Salt, FR-INV1

To a cooled solution of 48.0 g methylphosphonic acid (500 mmol) in 210 ml deionized water is slowly added 27.0 g aluminum ethoxide (167 mmol) under nitrogen. The reaction is then allowed to warm to room temperature and stirred for 16 h then concentrated and dried at 100° C. in vacuo to afford a clear, colorless solid. The solid was heated for 4 h at 280° C. resulting in an off-white solid that is stable to >400° C. Elemental anal: 31.5% P, 9.0% Al.

Formulations comprising the flame retardant from Example 1 are compounded with glass into polyamide 66 (Polynil® P50/2, mp 258° C.) and high melting polyamide 66T/66 formed from hexamethylene diamine and a 55:45 molar ration of terephthalic acid and adipic acid (Zytel@HTN 502, mp 304° C.), using a Leistriz 18 mm twin screw extruder and molded with a Van Dorn 35 ton injection molder into 1/32" bars which were subjected to the standard UL 94 Vertical Burn Test. Formulations and results are listed in Table 1 below.

TABLE 1

Burn Test Results in Glass Reinforced Polyamide Resin.

| | Formulation | | | | |
|---|---|---|---|---|---|
| | 1 | 2 | 3 | 4 | 5 |
| Nylon 88 | 45 | — | — | — | — |
| Nylon 6T/66 | — | 50 | 48 | 56 | 58 |
| Glass | 30 | 30 | 30 | 30 | 30 |
| FR-INV1 | 25 | 20 | 17 | 14 | 12 |
| Melem | 0 | 0 | 5 | 0 | 0 |
| UL-94 | Fail | V-0 | V-0 | V-0 | V-1 |

The flame retardant of the invention displays a surprisingly high efficiency in the high temperature polyamide when compared to the performance in PA66. It would be expected that the system could be further optimized with proper selection of synergist.

What is claimed:

1. A flame retardant, thermoplastic polymer composition comprising:
    a) a high temperature, thermoplastic polyamide that melts above 270° C., into which high temperature, thermoplastic polyamide has been compounded at temperatures above 270° C.
    b) from 1% to 24%, by weight based on the total weight of the flame retardant polymer composition, of a flame retardant material obtained by transforming one or more than one compound of formula (I) into a different material via a process comprising heating in the absence of other materials at temperatures of about 200° C. or higher from about 0.01 hour to about 20 hours the one or more than one compound of formula (I)

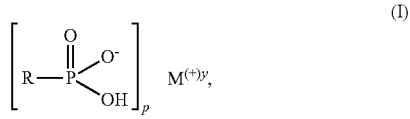

wherein
R is $C_{1-12}$ alkyl, $C_{6-10}$ aryl, $C_{7-18}$ alkylaryl, or $C_{7-18}$ arylalkyl, wherein said alkyl, aryl, alkylaryl, or arylalkyl are unsubstituted or are substituted by hydroxyl, amino, $C_{1-4}$ alkylamino, di-$C_{1-4}$ alkylamino, $C_{1-4}$ alkoxy, carboxy or $C_{2-5}$ alkoxycarbonyl;
M is a metal,
y is a number of from 1 to 4 so that $M^{(+)y}$ is a metal cation where (+)y represents the charge formally assigned to the cation, and p is a number of from 1 to 4, wherein the flame retardant, thermoplastic polymer composition is moldable.

2. The flame retardant, thermoplastic polymer composition according to claim 1 wherein M in formula (I) is Li, K, Na, Mg, Ca, Ba, Zn, Zr, B, Al, Si, Ti, Sn or Sb.

3. The flame retardant, thermoplastic polymer composition according to claim 1 wherein M in formula (I) is Al or Ca.

4. The flame retardant, thermoplastic polymer composition according to claim 1 wherein in formula (I) R is unsubstituted $C_{1-6}$ alkyl, $C_6$ aryl, $C_{7-10}$ alkylaryl, or $C_{7-12}$ arylalkyl.

5. The flame retardant, thermoplastic polymer composition according to claim 4 wherein R is methyl, ethyl, propyl, isopropyl, benzyl or phenyl.

6. The flame retardant, thermoplastic polymer composition according to claim 5 wherein M in formula (I) is Al or Ca.

7. The flame retardant, thermoplastic polymer composition according to claim 1 wherein the flame retardant material (b) is obtained by a process comprising:
    i) preparing an intermediate salt complex by treating one or more phosphonic acid compound with one or more appropriate metal compound to give an intermediate salt complex corresponding to formula (I) comprising multiple values for R and/or M, and then heating in the absence of other materials the intermediate salt complex at temperatures of about 200° C. or higher for about 0.01 hour to about 20 hours;
    or
    ii) preparing an intimate salt mixture by combining two or more individual metal phosphonic acid salts of formula (I) which have differing values for R and/or M, and then heating in the absence of other materials the intimate salt mixture at temperatures of about 200° C. or higher for about 0.01 hour to about 20 hours;
    or
    (iii) heating in the absence of other materials at temperatures of about 200° C. or higher for about 0.01 hour to about 20 hours two or more separate metal phosphonic acid salts of formula (I), which differ by having different values for R and/or M to form individual flame retardant materials that are subsequently mixed together to form a blended flame retardant material.

8. The flame retardant, thermoplastic polymer composition according to claim 1 wherein the flame retardant material of b) is obtained by a process comprising heating in the absence of other materials one or more than one compound of formula (I) at temperatures about 220° C. or higher for from about 0.01 hour to about 20 hours.

9. The flame retardant, thermoplastic polymer composition according to claim 1 wherein the thermoplastic polyamide of a) melts at temperatures of 280° C. or higher.

10. The flame retardant, thermoplastic polymer composition according to claim 1 further comprising a reinforcing agent.

11. The flame retardant, thermoplastic polymer composition according to claim 1 wherein the thermoplastic polyamide of a) is a glass filled thermoplastic polyamide.

12. The flame retardant, thermoplastic polymer composition according to claim 1, wherein the thermoplastic polyamide of a) comprises polyamide 46, polyamide 4T; polyamide MXD,6; polyamide 12,T; polyamide 10,T; polyamide 9,T; polyamide 6,T/6,6; polyamide 6,T/D,T; polyamide 6,6/6,T/6,I; polyamide 6/6,T; or polyamide 6,T/6,I.

13. The flame retardant, thermoplastic polymer composition according to claim 12 wherein the thermoplastic polyamide of a) is glass filled.

14. The flame retardant, thermoplastic polymer composition according to claim 1 further comprising (c) one or more compounds selected from the group consisting of additional flame retardants, synergists and flame retardant adjuvants.

15. The flame retardant, thermoplastic polymer composition according to claim 14, wherein the one or more additional flame retardants comprise alkyl or aryl phosphine oxide flame retardants, or salts of alkyl or aryl phosphinic acid.

16. The flame retardant, thermoplastic polymer composition according to claim 15 wherein the one or more additional flame retardants comprise an aluminum tris(dialkylphosphinate).

17. The flame retardant, thermoplastic polymer composition according to claim 14 comprising one or more synergists or flame retardant adjuvants, wherein the one or more synergists or flame retardant adjuvants comprise thermally compatible melamine derivatives, melamine condensation products, melamine salts, phosphine oxides, polyphosphine oxides, or metal hydroxides, oxides, oxide hydrates, borates, phosphates, phosphites or silicates.

18. A flame retardant, thermoplastic composition according to claim 17 wherein the one or more synergists or flame retardant adjuvants comprise aluminum hydrogen phosphite, benzylic phosphine oxides, poly benzylic phosphine oxides, melam, melem or melamine metal phosphate wherein the metal comprises aluminum, zinc or magnesium.

19. The flame retardant, thermoplastic polymer composition according to claim 14 comprising (c) one or more additional flame retardant, synergist or flame retardant adjuvant, wherein the one or more additional flame retardant, synergist or flame retardant adjuvant comprises an aluminum tris(dialkylphosphinate), aluminum hydrogen phosphite, methylene-diphenylphosphine oxide-substituted polyaryl ether, xylylenebis(diphenylphosphine oxide), 1,2-bis-(9,10-dihydro-9-oxy-10-phosphaphenanthrene-10-oxide) ethane, a 4,4'-bis(diphenylphosphinylmethyl)-1,1'-biphenyl, melam, melem, or dimelamine zinc pyrophosphate.

20. The flame retardant, thermoplastic polymer composition according to claim 1 wherein the thermoplastic polyamide of a) comprises monomers containing aromatic groups.

* * * * *